(12) United States Patent
Lo et al.

(10) Patent No.: US 8,547,548 B1
(45) Date of Patent: Oct. 1, 2013

(54) FINAL DEFECT INSPECTION SYSTEM

(71) Applicant: Kinsus Interconnect Technology Corp., Taoyuan (TW)

(72) Inventors: Chia-Chi Lo, Taoyuan County (TW); Cheng-Hsiung Yang Yang, Hsinchu (TW); Jun-Chung Hsu, Taoyuan County (TW)

(73) Assignee: Kinsus Interconnect Technology Corp., Taoyuan (TW)

( * ) Notice: Subject to any disclaimer, the term of this patent is extended or adjusted under 35 U.S.C. 154(b) by 0 days.

(21) Appl. No.: 13/721,019

(22) Filed: Dec. 20, 2012

(51) Int. Cl.
*G01N 21/00* (2006.01)

(52) U.S. Cl.
USPC ................... 356/237.5; 356/237.1; 356/237.4

(58) Field of Classification Search
USPC ............. 356/237.1–237.5, 388–394; 378/58, 378/98, 901; 382/8, 101, 106
See application file for complete search history.

(56) References Cited

U.S. PATENT DOCUMENTS

| | | | | |
|---|---|---|---|---|
| 5,204,912 A | * | 4/1993 | Schimanski | 382/147 |
| RE35,423 E | * | 1/1997 | Adams et al. | 378/58 |
| 6,021,380 A | * | 2/2000 | Fredriksen et al. | 702/35 |
| 2002/0083581 A1 | * | 7/2002 | Huber | 29/740 |
| 2010/0122634 A1 | * | 5/2010 | Doyle | 101/126 |

* cited by examiner

*Primary Examiner* — Sang Nguyen

(57) ABSTRACT

Disclosed is a final defect inspection system, which including a host device, a microscope, a bar code scanner, a support tool, a signal transceiver and an electromagnetic pen. The bar code scanner scans a bar code on a circuit board provided on the support plate. The host device selects data and a circuit layout diagram from the database corresponding to the bar code. The signal transceiver and the electromagnetic pen are electrically connected to the host device. The electromagnetic pen is used to make a mark on a scrap region of the circuit board where any defect is visually found through the microscope. The signal transceiver receives and transmits the positions of the mark to the host device such that the host device calculates the coordinate of a scrap region based on a relative position between an original point and the positions of the mark.

16 Claims, 4 Drawing Sheets

FINAL DEFECT INSPECTION SYSTEM

BACKGROUND OF THE INVENTION

1. Field of the Invention

The present invention generally relates to a final defect inspection system, and more specifically to a final defect inspection system using a signal transceiver to intuitively and directly mark the scrap regions so as to avoid mark error.

2. The Prior Arts

A traditional final inspection for circuit boards as a final check for shipping is performed after optical inspection by manually and visually inspecting the inspection regions preset on each circuit board through the microscope or magnifying glass. In the current manual processes, the operator usually uses a black pen or white paint pen to mark a scrap region where any defect is found. Each marked scrap region is provided for the subsequent laser marking process after the drying process, and used to generate the electronic file for recoding the scrap regions with defects. However, there are several problems occurring when the defect record is implemented by the electronic file. Firstly, automatic process and management are not implemented and potential risk always exists in the manual inspection because the operator needs to open the layout diagram with respect to the circuit board and simultaneously input the position of the scrap region to the computer. Secondly, as the circuit board becomes finer and more compact, the number of the inspection regions on the circuit board increases and the operator has to check the scrap regions by counting the columns and rows of the inspection regions such that some of the manually marked positions do not match those input to the computer. Thirdly, the mark manually specified for the scrap region by the traditional black pen and white paint pen tends to fall off and thus possibly causes serious pollution for the circuit board.

In general, the circuit boards through the final inspection will be delivered to the customer. If there are some defective circuit boards not excluded in the final inspection, the final products using the defective circuit boards become scrap products due to the mismatched record for the defect marks and serious pollution from the fallen marks. As a result, the customer may suffer significant loss and the credit in the market will be adversely influenced. Therefore, it needs a final defect inspection system to reduce the time of inspection and avoid mark error so as to overcome the problems in the prior arts.

SUMMARY OF THE INVENTION

Therefore, the present invention has been made in view of the above problems, and it is an object of the present invention is to provide a final defect inspection system, which comprises a host device, a microscope, a bar code scanner, a support tool, a signal transceiver and an electromagnetic pen. The final defect inspection system is provided for manually inspecting each inspection region on the circuit board and making marks on the scrap regions where any defect is found before shipment of the circuit board.

The host device has a database, which stores circuit layout diagrams of the circuit boards. The support tool is used to support one circuit board. The microscope comprises an eye lens, at least one object lens, a support plate and a support frame. The support plate is movable and used to support the support tool. The eye lens and the at least one object lens are used to inspect the inspection regions preset on the circuit board. The eye lens and the at least one object lens are jointed with the support plate through the support frame. The bar code scanner is electrically connected to the host device, and is used to scan a bar code on a circuit board. The host device selects data and a circuit layout diagram from the database corresponding to the bar code scanned. The signal transceiver is electrically connected to the host device and provided on the support tool. The electromagnetic pen is electrically connected to the signal transceiver and the host device.

After the bar code scanner scans the bar code and the host device selects data and the circuit layout diagram corresponding to the bar code scanned, the electromagnetic pen is used to specify original mark positions on the edges of the circuit board. For instance, the electromagnetic pen scribes one diagonal line on the circuit board to generate two original mark positions at two ends of the diagonal line. The signal transceiver receives and transmits the original mark positions to the host device. The host device defines an outline of the circuit board based on the original mark positions and the circuit layout diagram, and specifies one point on the circuit board as the original point. The microscope is used to inspect whether any defect exists in the inspection regions on the circuit board provided on the support tool. The electromagnet pen is used to make a mark on a scrap region where any defect is found. The signal transceiver receives and transmits the position of the mark to the host device such that the host device calculates a coordinate of a scrap region based on a relative position between the original point and the position of the mark, and generates a shipment file containing the coordinate of the scrap region.

Alternatively, the electromagnetic pen is replaced by a signal transmitter fixed on the support plate of the microscope and a foot pedal electrically connected to the signal transmitter 55. At this time, the final defect inspection system needs mechanic calibration before inspecting the circuit board.

The present invention uses the host device, the bar code scanner, the signal transceiver and the electromagnetic pen (or the combination of the signal transmitter and the foot pedal) to automatically read the data related to the circuit board and to calculate the marked scrap region so as to avoid data input error and data mismatch problem for the marked position and the input data. Therefore, the traditional black pen and the white paint pen are replaced and the risk of pollution for the processing circuit board is improved.

BRIEF DESCRIPTION OF THE DRAWINGS

The present invention can be understood in more detail by reading the subsequent detailed description in conjunction with the examples and references made to the accompanying drawings, wherein.

DETAILED DESCRIPTION OF THE PREFERRED EMBODIMENT

The present invention may be embodied in various forms and the details of the preferred embodiments of the present invention will be described in the subsequent content with reference to the accompanying drawings. The drawings (not to scale) show and depict only the preferred embodiments of the invention and shall not be considered as limitations to the scope of the present invention. Modifications of the shape of the present invention shall too be considered to be within the spirit of the present invention.

Figure 1:
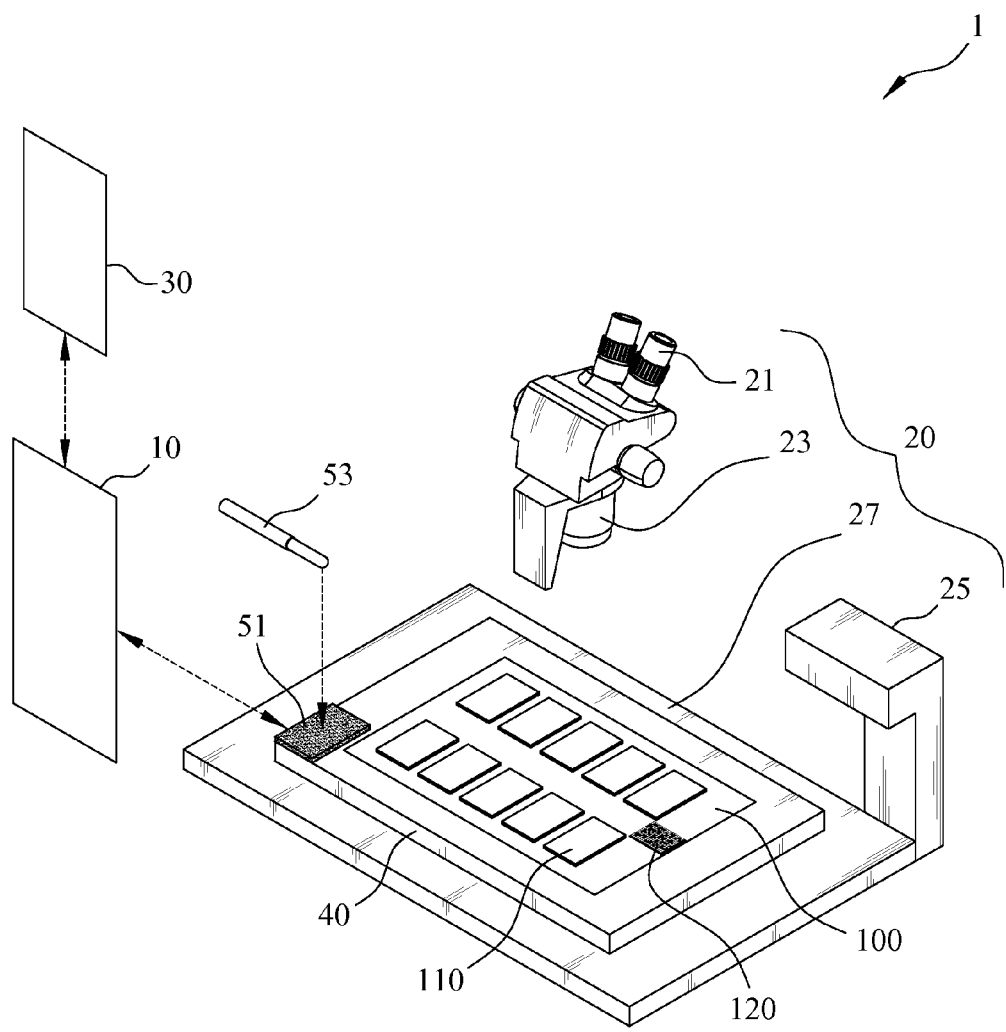
FIG. 1 is a view showing the final defect inspection system according to the first embodiment of the present invention.

Please refer to FIG. 1 for illustrating the final defect inspection system according to the first embodiment of the present invention. As shown in FIG. 1, the final defect inspection system 1 of the present invention comprises a host device 10, a microscope 20, a bar code scanner 30, a support tool 40, a signal transceiver 51 and an electromagnetic pen 53. The final defect inspection system 1 is provided for manually inspecting each inspection region 110 on the circuit board 100 and indicating a scrap region before shipment of the circuit board 100.

The host device 10 has a database, which stores data and layout diagrams. The bar code scanner 30 is electrically connected to the host device 10, and used to scan the bar code 120 on the circuit board 100. The host device 10 selects data and a circuit layout diagram from the database corresponding to the bar code 120.

The microscope 20 comprises an eye lens 21, at least one object lens 23, a support plate 25 and a support frame 27. The eye lens 21 has a magnification of 10× to 100×, and the at least one object lens 23 has a magnification of 1× to 10×. The support plate 25 is movable and used to support the support tool 40. The eye lens 21 and the at least one object lens 23 are used to inspect the inspection regions preset on the circuit board 100. The eye lens 21 and the at least one object lens 23 are jointed with the support plate 25 through the support frame 27.

The signal transceiver 51 is provided on the support tool 40, and electrically connected to the host device 10 and the electromagnetic pen 53. The electromagnetic pen 53 make a mark on the scrap region where any defect is found through the microscope 20, and the signal transceiver 51 receives and transmits each defect position to the host device 10.

Specifically, during the operation of the final defect inspection system 1 of the present invention, the bar code scanner 30 first scans the bar code 120 on the circuit board 100. The host device 10 selects data and the circuit layout diagram from the database of the circuit board 100 corresponding to the bar code 120 scanned. Then, the electromagnetic pen 53 is used to specify and mark the original mark positions on the edges of the circuit board 100, such as at least two points (for instance, the upper-left and lower-right points) on the diagonal line on the circuit board 100. The signal transceiver 51 receives and transmits the original mark positions to the host device 10. The host device 10 defines an outline of the circuit board 100 based on the original mark positions and the circuit layout diagram, and specifies one point on the circuit board 100 as the original point. Next, the circuit board 100 provided on the support tool 40 is visually inspected through the microscope 20. The electromagnetic pen 53 makes a mark on the scrap region where any defect is visually found. The signal transceiver 51 receives and transmits the position of the mark to the host device 10 such that the host device 10 calculates a coordinate of a scrap region based on a relative position between the original point and the position of the mark, and generates a shipment file containing the coordinate of the scrap region.

The host device 10 is electrically connected to the bar code scanner 30 and the signal transceiver 51 through wired or wireless connection. The wireless connection is preferably implemented by BLUETOOTH™ or wireless LAN (local area network). Similarly, the signal transceiver 51 and the electromagnetic pen 53 are connected through wired or wireless connection, and the wireless connection is preferably implemented by ultrasonic waves, BLUETOOTH™ or infrared rays.

Figure 2:
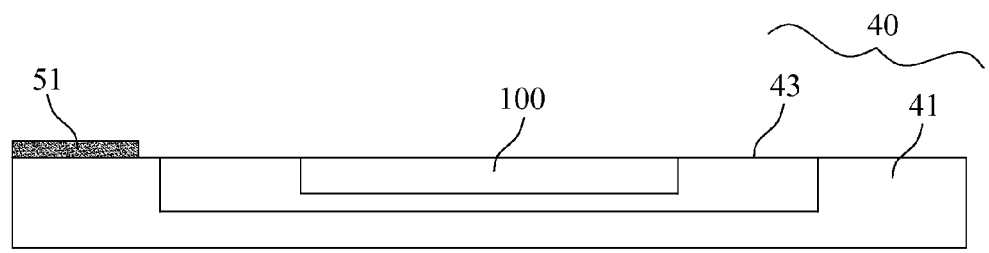
FIG. 2 is a cross-sectional view showing the support tool in FIG. 1.

Refer to FIG. 2 showing the cross section of the support tool 40 in FIG. 1. As shown in FIG. 2, the support tool 40 comprises a base 41 and a support piece 43. The base 41 has a recess part to accommodate the substrate plate 43, and similarly the support piece 43 has a recess part to support the circuit board 100. The substrate plate 43 can be replaced according to the size and shape of the circuit board 100, and the signal transceiver 51 is provided on the base 41.

Figure 3:
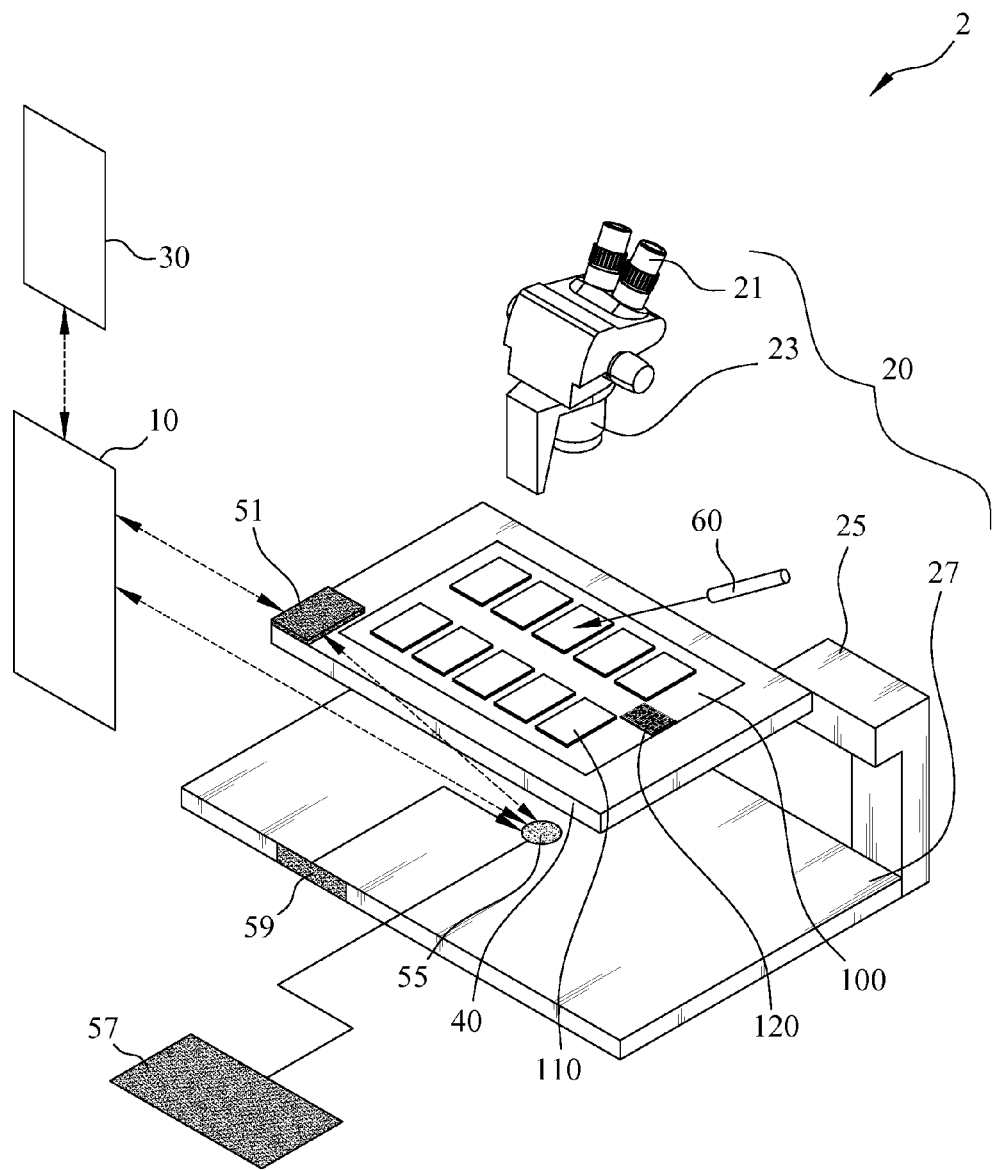
FIG. 3 is a view showing the final defect inspection system according to the second embodiment of the present invention.

Further refer to FIG. 3 for illustrating the final defect inspection system according to the second embodiment of the present invention. As shown in FIG. 3, the final defect inspection system 2 of the second embodiment is slightly modified from the final defect inspection system 1 in FIG. 1, and comprises a host device 10, a microscope 20, a bar code scanner 30, a support tool 40, a signal transceiver 51, a signal transmitter 55, a foot pedal 57 and a battery 59. It is noted that the host device 10, the microscope 20, the bar code scanner 30 and the support tool 40 are the same as those of the final defect inspection system 1, and the detailed description is thus omitted. The signal transmitter 55 is provided on the support plate 27 of the microscope 20, and electrically connected to the signal transceiver 51 and the host device 10. The foot pedal 57 is electrically connected to the signal transmitter 55. The battery 59 is used to supply electrical power for the signal transmitter 55, and provided on the support plate 27 of the microscope 20.

The signal transmitter 55 is electrically connected to the foot pedal 57 and the host device 10 through wired or wireless connection. Preferably, the wireless connection between the signal transmitter 55 and the foot pedal 57 is implemented by ultrasonic waves, BLUETOOTH™ or infrared rays, and the wireless connection between the signal transmitter 55 and the host device 10 is implemented by BLUETOOTH™ or LAN.

Figure 4:
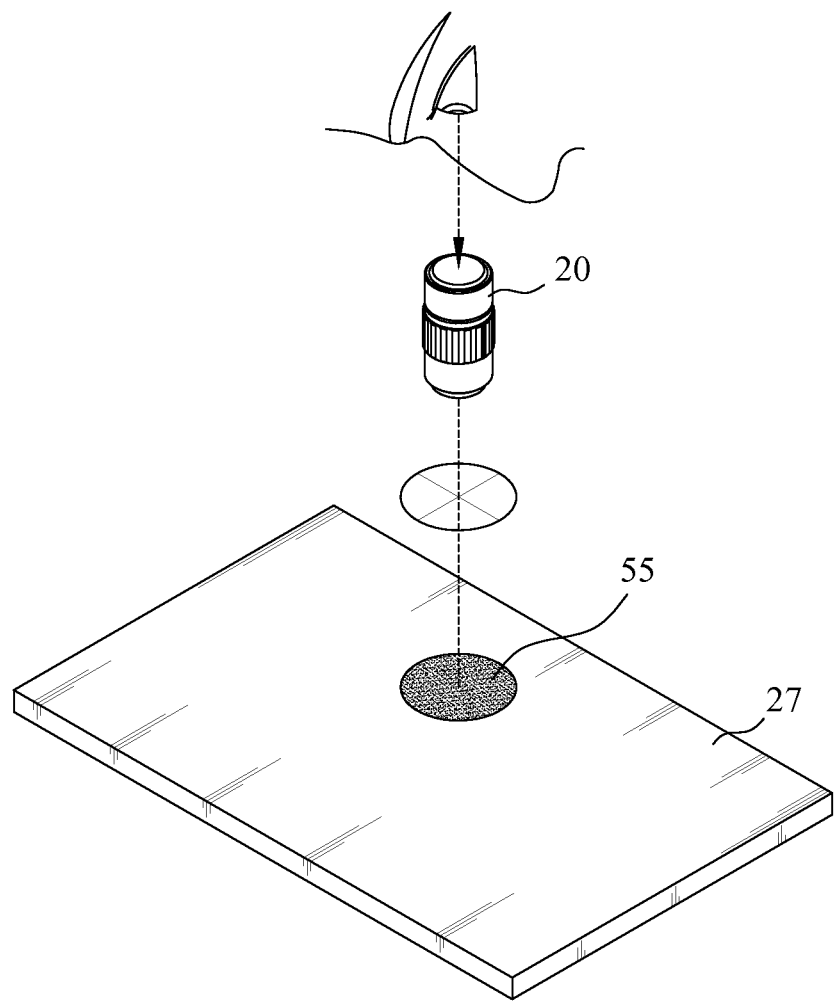
FIG. 4 is a view showing the final defect inspection system in FIG. 3 under calibration.

Meanwhile, refer to FIG. 4 for illustrating the final defect inspection system in FIG. 3 under mechanic calibration. As shown in FIGS. 3 and 4, the operation of the final defect inspection system 2 begins by aligning a cross mark region seen from the microscope 20 and the signal transmitter 55, and then stamping the foot pedal 57 such that the microscope 20 is positioned to correspond with the signal transmitter 55. At this time, the signal transmitter 55 transmits a positioning signal to the host device 10, thereby finishing the mechanic calibration. Then, the bar code scanner 30 scans the bar code 120 on the circuit board 100 provided on the support tool 40. The host device 10 reads the data and the layout diagram based on the bar code 120 scanned. The support plate 27 of the microscope 20 is moved until the cross mark region is aligned with the two points (such as the upper-left and lower-right points) on the diagonal line on the circuit board 100 provided on the support tool 40 as the original aligned positions. Then, the foot pedal 57 is stamped. At this time, the signal transceiver 51 receives and transmits the original aligned positions to the host device 10 such that the host device 100 defines an outline of the circuit board 100 based on the original mark positions and the circuit layout diagram, and specifies one point on the circuit board as the original point. Next, the foot pedal 57 is stamped to generate defect aligned positions when the cross mark region seen from the microscope 20 aligns each defect position where any defect is visually found on the inspection regions 110 through the microscope 20. The signal transceiver 51 receives and transmits each defect position to the host device 10. The host device 10 calculates each coordinate of the scrap region based on a relative position between an original point and each defect position, and stores each coordinate of the scrap region in a shipment file.

Additionally, the final defect inspection system 2 of the present invention may further comprise a laser pen provided on the support frame 27 of the microscope 20 to generate a light spot used to enhance illumination intensity. Therefore, in addition to aligning the cross mark region seen from the microscope 20 and the signal transmitter 55, the light spot is also needed to align the cross mark region such that the foot pedal 57 is stamped to finish the calibration of positioning.

Apparently from the above detailed description for the present invention, one aspect of the present invention is that it is possible to automatically read the data related to the circuit board and to calculate the marked defect position by using the host device, the bar code scanner, the signal transceiver and the electromagnetic pen. Also, data input error and data mismatch problem for the manually marked position and the data input to the computer are avoided.

Another aspect of the present invention is that those problems about data input error and data mismatch problem for the manually marked position and the data input to the computer can be avoided through the host device, the bar code scanner, the signal transceiver, the signal transmitter and the foot pedal. Thus, the traditional black pen and white paint pen are thus totally replaced and the risk of pollution for the processing circuit board is greatly improved.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A final defect inspection system, comprising:
a host device having a database, which stores circuit layout diagrams of circuit boards;
a support tool supporting one circuit board to be inspected;
a microscope comprising an eye lens, at least one object lens, a support plate and a support frame, wherein the support plate is movable and supports the support tool, the eye lens and the at least one object lens are used to inspect inspection regions preset on the circuit board, and the eye lens and the at least one object lens are jointed with the support plate through the support frame;
a bar code scanner electrically connected to the host device and scanning a bar code on the circuit board, wherein the host device selects data and one circuit layout diagram from the database corresponding to the bar code;
a signal transceiver provided on the support tool and electrically connected to the host device; and
an electromagnetic pen electrically connected to the signal transceiver,
wherein the electromagnet pen makes a mark a scrap region where any defect is found through the microscope, the signal transceiver receives and transmits each position of the mark to the host device, and the host device calculates each coordinate of the scrap region based on a relative position between the original point and each position of the mark, and stores each coordinate of the scrap region in a shipment file.

2. The final defect inspection system as claimed in claim 1, wherein the electromagnetic pen scribes one diagonal line on the circuit board and generates at least two original mark positions on edge of the circuit board after the bar code scanner scans the bar code and the host device selects data and the circuit layout diagram corresponding to the bar code scanned, the at least two original mark positions comprises two positions at two ends of the diagonal line, the signal transceiver receives and transmits the original mark positions to the host device, and the host device defines an outline of the circuit board based on the original mark positions and the circuit layout diagram, and specifies one point on the circuit board as the original point.

3. The final defect inspection system as claimed in claim 1, wherein the eye lens has a magnification of 10× to 100×, and the at least one object lens has a magnification of 1× to 10×.

4. The final defect inspection system as claimed in claim 1, wherein the host device and the bar code scanner are connected through wired or wireless connection, and the host device and the signal transceiver are connected through wired or wireless connection.

5. The final defect inspection system as claimed in claim 4, wherein the wireless connection is implemented by wireless LAN (local area network).

6. The final defect inspection system as claimed in claim 4, wherein the signal transceiver and the electromagnetic pen are connected through wired or wireless connection, and the wireless connection is implemented by ultrasonic waves, or infrared rays.

7. The final defect inspection system as claimed in claim 1, wherein the support tool comprises a base and a support piece, the base has a recess part to accommodate the substrate plate, and the support piece has a recess part to support the circuit board.

8. A final defect inspection system, comprising:
a host device having a database, which stores circuit layout diagrams of circuit boards;
a support tool supporting one circuit board to be inspected;
a microscope comprising an eye lens, at least one object lens, a support plate and a support frame, wherein the support plate is movable and supports the support tool, the eye lens and the at least one object lens are used to inspect inspection regions preset on the circuit board, and the eye lens and the at least one object lens are jointed with the support plate through the support frame;
a bar code scanner electrically connected to the host device and scanning a bar code on the circuit board, wherein the host device selects data and one circuit layout diagram from the database corresponding to the bar code;
a signal transceiver provided on the support tool and electrically connected to the host device;
a signal transmitter provided on the support plate of the microscope and electrically connected to the host device; and
a foot pedal connected to the signal transmitter,
wherein the foot pedal is stamped to generate defect aligned positions when a cross mark region seen from the microscope aligns each defect position where any defect is visually found on the inspection regions through the microscope, the signal transceiver receives and transmits each defect position to the host device, and the host device calculates each coordinate of a scrap region based on a relative position between an original point and each defect position, and stores each coordinate of the scrap region in a shipment file.

9. The final defect inspection system as claimed in claim 8, wherein the foot pedal is stamped when the signal transmitter and a cross mark region seen from the microscope are aligned such that the microscope is positioned to correspond with the signal transmitter, the signal transmitter transmits a positioning signal to the host device, the support plate of the microscope is moved until the cross mark region seen from the microscope is aligned with two points of at two ends of the diagonal line on the circuit board such that the foot pedal is stamped to generate original aligned positions, the signal transceiver receives and transmits the original aligned positions to the host device, and the host device defines an outline of the circuit board based on the original aligned positions and the circuit layout diagram, and specifies one point on the circuit board as the original point.

10. The final defect inspection system as claimed in claim 8, wherein the support tool comprises a base and a support piece, the base has a recess part to accommodate the substrate plate, and the support piece has a recess part to support the circuit board.

11. The final defect inspection system as claimed in claim 8, further comprising a laser pen provided on a support frame of the microscope to generate a light spot used to enhance illumination intensity, wherein the light spot is used to align the cross mark region and the signal transmitter, and then the foot pedal is stamped to finish calibration positioning.

12. The final defect inspection system as claimed in claim 8, wherein the eye lens has a magnification of 10× to 100×, and the at least one object lens has a magnification of 1× to 10×.

13. The final defect inspection system as claimed in claim 8, wherein the host device is connected to the bar code scanner, the signal transceiver, and the signal transmitter through wired or wireless connection.

14. The final defect inspection system as claimed in claim 13, wherein the wireless connection is implemented by wireless LAN.

15. The final defect inspection system as claimed in claim 8, further comprising a battery provided on the support plate of the microscope to supply electric power for the signal transmitter.

16. The final defect inspection system as claimed in claim 8, wherein the signal transceiver and the signal transmitter are connected through wired or wireless connection, and the wireless connection is implemented by ultrasonic waves, or infrared rays.

* * * * *